United States Patent [19]

Lucas et al.

[11] 4,035,506
[45] July 12, 1977

[54] FLUOROCARBON DERMAL PROTECTIVE COMPOSITIONS

[75] Inventors: Anthony James Lucas, Oakdale; Peter John Degen, Woodbury Township, Washington County both of Minn.

[73] Assignee: Minnesota Mining and Manufacturing Company, St. Paul, Minn.

[21] Appl. No.: 492,200

[22] Filed: July 26, 1974

[51] Int. Cl.² ................................ A61K 31/255
[52] U.S. Cl. .................... 424/303; 424/205; 424/311; 424/312; 424/313; 424/320; 424/321; 424/336; 260/399; 260/400; 260/401; 260/403; 260/407; 260/408; 260/455 R; 260/456 A; 260/458 R; 260/468 R; 260/469; 260/476 R; 260/481 R; 260/482 R; 260/484 B; 260/485 F; 260/486 R; 260/487; 260/468 L; 260/488 H; 260/488 J; 260/455 A; 260/607 AL
[58] Field of Search ............... 424/312, 303, 313

[56] References Cited

U.S. PATENT DOCUMENTS

| | | | |
|---|---|---|---|
| 3,100,180 | 8/1963 | Smith et al. | 424/60 |
| 3,398,182 | 8/1968 | Guenthner | 260/455 |
| 3,541,205 | 11/1970 | Hardigan et al. | 424/60 |
| 3,636,085 | 1/1972 | Kleiner | 260/485 F |
| 3,736,300 | 5/1973 | Kleiner | 260/78.4 E |

*Primary Examiner*—Norman A. Drezin
*Attorney, Agent, or Firm*—Cruzan Alexander; Donald M. Sell; Carolyn A. Bates

[57] ABSTRACT

Dermal protective compositions are disclosed which comprise a pharmaceutical extending medium having incorporated therein a substantive, dermally non-irritating compound which is a polyfunctional organic molecule containing one or more fluorocarbon-containing groups joined by one or more polar linking groups to a polyvalent organic radical. When applied to skin, these compositions provide repellency against a wide variety of dermal irritants and are resistant to removal by mild abrasion and/or detergent solutions.

8 Claims, No Drawings

FLUOROCARBON DERMAL PROTECTIVE COMPOSITIONS

This invention relates to dermal protective compositions. More specifically, this invention relates to dermal protective compositions which are substantive to skin and which have the ability to render the skin repellent to a wide variety of chemical irritants. A further aspect of the invention relates to novel chemical compounds which comprise the preferred compositions of the invention.

Human skin is routinely exposed to a multiplicity of chemical irritants such as detergents, bleaches, organic solvents, oils and the like. Exposure to these irritants often results in damaging and/or unsightly skin conditions.

To protect the skin against the undesirable effects of common irritants, a number of chemical compositions are known which can be applied to the skin prior to exposure to irritants in order to minimize contact of the irritant with the skin.

Known skin-protective compositions generally utilize oligomeric or polymeric materials as protective agents, especially those based on hydrocarbon, slicon and/or fluorinecontaining materials. Protective compositions based on fluorocarbon elastomers are described in U.S. Pat. No. 3,100,180. Other compositions containing skin-protective agents based on both fluorine and silicon are described in U.S. Patent 3,541,205.

Polymerized fatty acids (dimer, trimer and tetramer acids) and their derivatives have been described as providing protection against skin irritation when added to detergents, cutting fluids, cleansing and other irritant-containing compositions. These agents are termed "mildness additives" and are described in U.S. Pat. Nos. 3,538,009, 3,630,934, 3,798,182 and 3,818,350.

Polymerized fatty acid derivatives, including some compounds containing ester and amide linkages, are described in Netherlands Pat. No. 7,114,005 as skin protective agents. These compounds are formulated into compositions for topical application and are thought to manifest their skin-protecting effects by physiological means. By providing additional bridges between the protein molecules of the keratin layer of the skin, these compounds are believed to preserve the integrity of the skin surface and thereby prevent penetration by irritants.

In general, skin protective compositions have heretofore been unsuccessful in providing truly effective protection for the skin against the effects of exposure to harsh irritants. Many skin creams, lotions and various emollient compositions are largely intended to exert a beautifying or moisturizing effect and, while imparting an immediate pleasant feeling or appearance, offer little or no prolonged protection against irritation. Even protective compositions which are so-called "long-lasting" are often readily removed by warm detergent solutions and require repeated applications for sustained protection.

In addition, most protective or "barrier" skin creams have heretofore been selective in providing protection against one or a few chemical irritants and have failed to gain broad general applicability. Another disadvantage of certain prior art compositions is that they are difficult to formulate into cosmetically acceptable forms. This problem is especially associated with protective agents based on polymeric materials and those containing fluorine and silicon. Silicon materials are often greasy and easily transferred to other substrates upon contact. Compositions containing paraffin derivatives are also extremely greasy and unpleasant to apply.

The disadvantages associated with skin protective compositions of the prior art are largely eliminated by the dermal protective compositions of the present invention.

The present invention provides dermal protective compositions comprising a substantive, dermally non-irritating, fluorocarbon-containing, multipolar organic compound incorporated into suitable pharmaceutical extending medium. These compositions possess unique skin protective and cosmetic properties. Compositions of the present invention are substantive to skin, adhering with extreme tenacity even after abrasion and prolonged challenges with hot aqueous soap and detergent solutions. These compositions provide effective protection to the skin against a wide variety of potential chemical irritants such as detergents, bleaches, oils, solvents and other skin-damaging chemicals by providing a repellent barrier to the irritant. In addition, compositions of the present invention are readily formulatable into a variety of cosmetically-appealing, non-tacky and non-greasy topical preparations.

The active dermal protective agents comprising the compositions of the invention are skin substantive, dermally non-irritating poly-functional organic molecules having at lease one fluorocarbon-containing group; two or more groups capable of electrostatic, hydrogen, covalent or ionic bonding with skin protein; and an aliphatic bridging group. These organic molecules are defined by the following general formula:

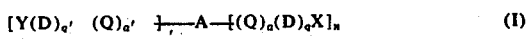

wherein A is a polyvalent saturated or unsaturated, aliphatic or cycloaliphatic organic radical containing 8 to 108 carbon atoms;

Q is $-NH$, $-O-$, or $-S-$;

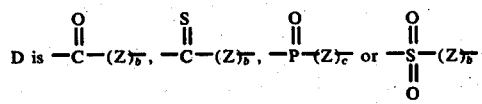

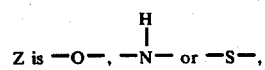

$b$ is zero or one, $c$ is zero, one or two, and when $c$ is two, each Z is attached to P;

X is $-(W)_dR_f$ where W is a bridging group;

$d$ is zero or one and $R_f$ is a fluorinated, saturated, monovalent, aliphatic radical of at least 3 carbon atoms;

Y is $-H$, $M^{e+}$ or $-R^1$ $R^1$ is an aliphatic, cycloaliphatic or aromatic radical containing 1 to 24 carbon atoms;

$M^{e+}$ is a pharmaceutically acceptable organic or inorganic cation, and $e$ is one, two or three;

$n$ is an integer from 1 to 10 designating the same or different $-[(Q)_a(D)_qX]$ $n'$ is zero or an integer from 1 to 9 designating the same different $-[(Q)_a \quad (D)_q \quad Y]$ $n + n' = 2 - 10$;

$a$ and $a'$ are independently zero or 1;

q is one; q' is zero or one;
said compound containing from 1 to 60 percent by weight of fluorine;
and a pharmaceutical extending medium compatible therewith.

The term "substantive" as used herein to describe the dermal protective compositions of the invention refers to the ability of these materials to retain at least 50 percent of their original repellent properties on a pigskin surface after a one-hour challenge with detergent solution.

The various combinations of Q and D in the above formula form the "polar linking groups" of the compounds of Formula 1 and function to connect the organic radical A with the fluorocarbon-containing group X and the non-fluorocarbon containing group Y when Y is present. These polar linking groups may be generally described as either ester, amide, urethane or urea groups. Compounds of Formula 1 containing these linking groups are prepared by conventional chemical reactions, well-known in the art, for preparing esters, amides, urethanes and ureas. The choice of starting materials is, therefore, dictated by the particular polar linking group desired in the final product. It is clear, for example, that reacting an alcohol with an acid will generate a compound having an ester linking group, reacting an acid with an amine will generate an amide, reacting an isocyanate with an alcohol will generate a urethane and so forth.

In general, compounds of the invention are prepared by the condensation of a polyfunctional aliphatic or cycloaliphatic compound containing 8 to 108 carbon atoms, which may or may not contain sites of unsaturation, (the unreactive portion of which forms the A-substituent of Formula 1), with a fluorocarbon-containing compound (the unreactive portion of which forms the X-substituent of Formula 1) having the appropriate functional group necessary to form the desired polar linking group QD between A and X. In addition to the above-described co-reactants, some of the compounds of the invention require a third co-reactant (the unreactive portion of which forms the Y-substituent of Formula 1). This third co-reactant must also contain the appropriate functional group necessary to form the desired polar linking group QD between A and Y.

Typical examples of starting materials from which the A-substituent is derived are given in the following Table I:

TABLE I

STARTING MATERIALS FROM WHICH THE A-FORMING SUBSTITUENT MAY BE SELECTED

| STRUCTURE | CHEMICAL NAME |
|---|---|
| ACIDS | |
| $HOOC-(CH_2)_8-COOH$ | decanedioic acid |
| $HOOC-(CH_2)_{10}-COOH$ | dodecandioic acid |
| $HOOC-(CH_2)_{11}-COOH$ | tridecanedioic acid |
| $HOOC-(CH_2)_{14}-COOH$ | hexadecanedioic acid |
| $HOOC-(A)-COOH$ | Hystrene ® 3695 "Dimer Acid" (A = aliphatic portion of a dimerized $C_{18}$ fatty acid) |
| $A-(COOH)_n$ | Empol ® 1056A "Polybasic Acid" (A = aliphatic portion of polymerized $C_{18}$ fatty acid, n = 2–6) |
| $HOOC-CH(C_{14}H_{29})-CH_2-COOH$ | tetradecylmaleic acid |
| $HOOC-CH(C_{20}H_{41})-COOH$ | eicosylmalonic acid |
| $HOOC-CH(C_{14}H_{29})-COOH$ | tetradecylmalonic acid |
| $HOOC\backslash C=CH(CH_2)_8-CH(CH_3)-(CH_2)_7-CH(CH_3)-(CH_2)_6-CH_3 / HOOC$ | 12, 15-dimethyl-docosene (1,2)-dicarboxylic acid (1,1) |
| $HOOC-(CH_2)_6-CH=CH-(CH_2)_{10}-COOH$ | eicosene (8) - dicarboxylic acid (1,20) |
| ALCOHOLS | |
| $HOH_2C-(CH_2)_8-CH_2OH$ | 1, 10-decanediol |

TABLE I-continued

STARTING MATERIALS FROM WHICH THE A-FORMING SUBSTITUENT MAY BE SELECTED

| STRUCTURE | CHEMICAL NAME |
|---|---|
| $HOH_2C(CH_2)_{10}CH_2OH$ | 1, 12-dodecanediol |
| $HOH_2C(CH_2)_{11}CH_2OH$ | 1, 13-tridecanediol |
| $HOH_2C(A)CH_2OH$ | reduced ® Hystrene 3695 (A = aliphatic portion of a dimerized $C_{18}$ fatty acid) |
| $A(CH_2OH)_n$ | reduced ® Empol 1056A (A = aliphatic portion of polymerized $C_{18}$ fatty acid, n = 2-6) |
| AMINES | |
| $H_2N(CH_2)_{12}NH_2$ | dodecane diamine |
| 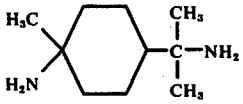 | menthane diamine |
| $H_2N(CH_2)_8NH_2$ | 1, 8 octane diamine |
| 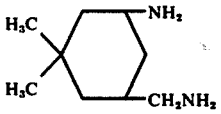 | isophorone diamine |
| $A(NH_2)_2$ | General Mills Brand "Modified Amine" A-100. (A = aliphatic portion of polymerized fatty acid) |
| MERCAPTANS | |
| $HS(CH_2)_8SH$ | 1, 8-octanedithiol |
| $HS(CH_2)_9SH$ | 1, 9-nonanedithiol |
| ISOCYANATES | |
| $OCN(CH_2)_{12}NCO$ | 1, 12-diisocyanate dodecane |
| 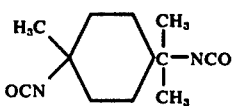 | diisocyanate menthane |
| 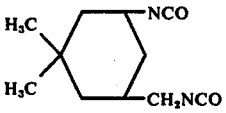 | diisocyanate isophorone |
| $OCN(A)NCO$ | General Mills Brand DDI ®-1410 (A = $C_{36}$ aliphatic radical) |
| $OCN(CH_2)_8NCO$ | 1, 8-diisocyanate octane |

The fluorocarbon-containing substituent X of Formula 1 is derived from known fluorocarbon starting materials. The W-portion of the X-substituent provides a bridging group between the QD polar linking group and the Rf or fluorocarbon group. This bridging group has little or no recognizable effect on the substantivity or repellent properties of the dermal protective agents. In fact, the W-portion may be entirely omitted. For ease of preparing compounds of Formula 1, it is desirable that the W-portion of X-substituent be free of isocyanate or isocyanate-reactive groups which may interfere with the formation of the polar linking group QD. In general, the X-forming substituent may be preferably selected from the following groups. (The $R_f$ group has been included to indicate its point of attachment.)

(1) $-(CH_2)_m^{}NSO_2R_f$ with $R^2$ on N (2) $-(CH_2)_m^{}N(R^2)-C(=O)-R_f$ (3) $-(CH_2)_m^{}SO_2R_f$ (4) $-(CH_2)_m^{}C(=O)-R_f$ (5) $-(CH_2)_m^{}R_f$ (6) $-C_{m'}H_{2m'-2}-R_f$ (7) $-(CH-CH_2-O)_{m''}(CH_2)_m^{}-NSO_2R_f$ with $R^3$ on CH and $R^2$ on N -continued (8) $-(CH-CH_2-O)_{m''}(CH_2)_{m}-\overset{O}{\underset{\|}{C}}-R_f$
    with $R^3$ on the CH (9) $-(CH-CH_2-O)_{m''}(CH_2)_{m}-R_f$
    with $R^3$ on the CH

(10) $-(CH_2-CH_2-CH_2-CH_2-O)_{m''}(CH_2)_{m}-R_f$

(11) $-CH_2-CH(Cl)-(CH_2)_{m}-R_f$

(12) $-(CH_2)_{m'}-O-(CH_2)_{m}-R_f$

(13) $-(CH_2)_{m}CH=CH-R_f$

(14) $-(CH_2)_{m'}-O-(CH_2)_{m}-CH=CH-R_f$

(15) phenyl ring substituted with $R_f$

(16) phenyl ring substituted with $-\overset{O}{\underset{\|}{C}}-R_f$

(17) phenyl ring substituted with $-OSO_2R_f$ $R^2$ is H or an alkyl radical containing 1–8 carbons
$R^3$ is H, $-CH_3$ or $-C_2H_5$
$m$ is an integer from 1 to 12
$m'$ is an integer from 2 to 12
$m''$ is an integer from 1 to 24

The Rf portion of the X-substituent is a fluorinated, saturated, monovalent, aliphatic radical of at least 3 carbon atoms. The chain may be straight, branched or, if sufficiently large, cyclic, and may be interrupted by divalent oxygen atoms or trivalent nitrogen atoms bonded only to carbon atoms. Preferably, the chain of the fluorinated radical does not contain more than one hetero atom, i.e., nitrogen or oxygen, for every two carbon atoms in the skeletal chain. A fully fluorinated group is preferred, but hydrogen or chlorine atoms may be present as substituents in the fluorinated aliphatic radical provided that not more than one atom of either is present in the radical for very two carbon atoms, and that radical must at least contain a terminal perfluoromethyl group. Preferably, Rf contains not more than 20 carbon atoms because such a large radical results in inefficient use of the fluorine content.

It is presently preferred that the X-substituent [or $-(W)_dR_f$] contain at least 25 percent by weight of fluorine. Typical examples of starting materials from which the X-substituent may be formed are given in the following Table II.

Table II

Fluorocarbon Starting Materials

Alcohols $HO-CH_2CH_2-\underset{CH_3}{N}SO_2C_8F_{17}$

Table II-continued $HO-CH_2(CH_2)_{10}-\underset{C_2H_5}{N}SO_2C_8F_{17}$ $HO-CH_2(CH_2)_7-\underset{C_4H_9}{N}SO_2C_{18}F_{37}$ $HO-CH_2CH_2-\overset{O}{\underset{\|}{C}}C_8F_{17}$ $HO-CH_2(CH_2)_{10}-\overset{O}{\underset{\|}{C}}C_8F_{17}$ $HO-CH_2(CH_2)_7-\overset{O}{\underset{\|}{C}}C_{16}F_{33}$ $HO-(CH_2CH_2O)_2-CH_2-C_8F_{17}$ $HO-(CH_2)_6-C_8F_{17}$ $HO-CH_2CH_2-\underset{\underset{\|}{O}}{\overset{C_2H_5}{N}}CC_8F_{17}$ $HO-(CH_2CH_2CH_2CH_2O)_2-CH_2-C_{18}F_{37}$ HO— phenyl ring —$OSO_2C_8F_{17}$ Mercaptans $HS-CH_2CH_2-\underset{CH_3}{N}SO_2C_8F_{17}$ $HS-CH_2(CH_2)_7-\underset{C_2H_5}{N}SO_2C_{12}F_{25}$ $HS-CH_2(CH_2)_{10}-\underset{C_4H_9}{N}SO_2C_{18}F_{37}$ $HS-CH_2(CH_2)_{10}-\underset{H}{N}-\overset{O}{\underset{\|}{C}}C_8F_{17}$ $HS-CH_2(CH_2)_7-\underset{H}{N}-\overset{O}{\underset{\|}{C}}C_{18}F_{37}$ $HS-CH_2(CH_2)_7-\overset{O}{\underset{\|}{C}}C_6F_{13}$ $HS-CH_2(CF_2)_2CH_2OC_8F_{17}$ $HS-CH_2(CF_2)_2CH_2OC_{12}F_{25}$ $HS-(CH_2)_{10}CHClCH_2C_8F_{17}$ $HS-(CH_2)_6CHClCH_2C_{18}F_{37}$ HS— phenyl ring —$OSO_2C_8F_{17}$ $HS-(CH_2CH_2-O)_2CH_2CH_2\underset{CH_3}{N}SO_2C_8F_{17}$ Amines $H_2N-CH_2CH_2-\underset{CH_3}{N}SO_2C_8F_{17}$ $H_2N-CH_2(CH_2)_{10}-\underset{C_4H_9}{N}SO_2C_{18}F_{37}$ Table II-continued

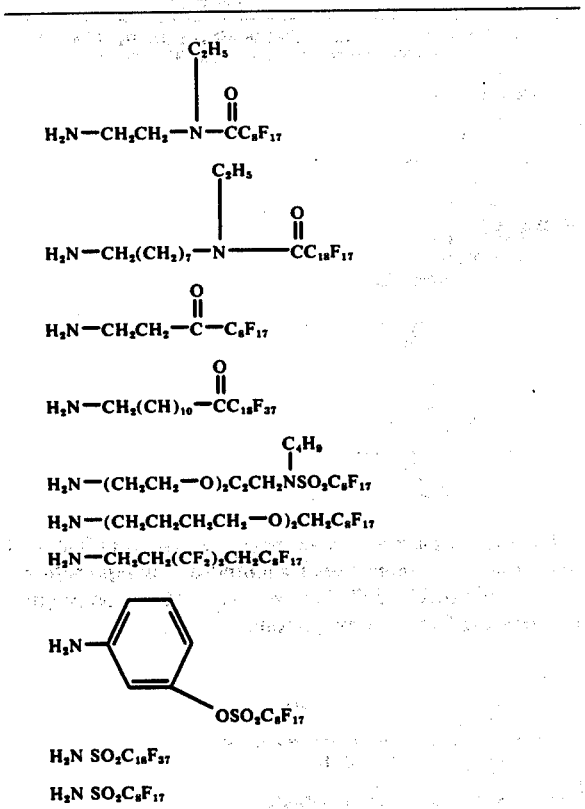

Phosphoric Acids and Phosphate Esters

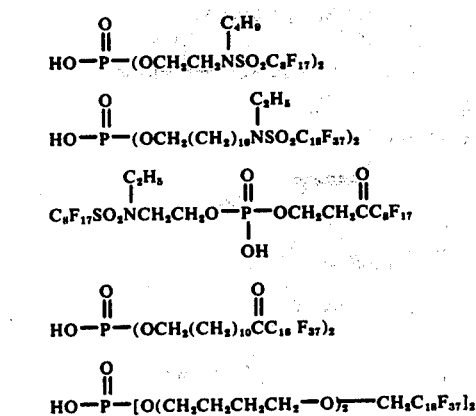

Acids

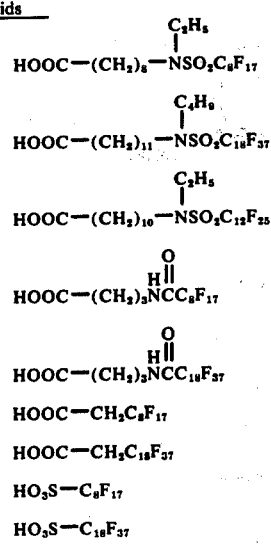

HOOC—CH₂C₈F₁₇

HOOC—CH₂C₁₈F₃₇

HO₃S—C₈F₁₇

HO₃S—C₁₈F₃₇

Table II-continued

HO₃S—C₆F₁₃

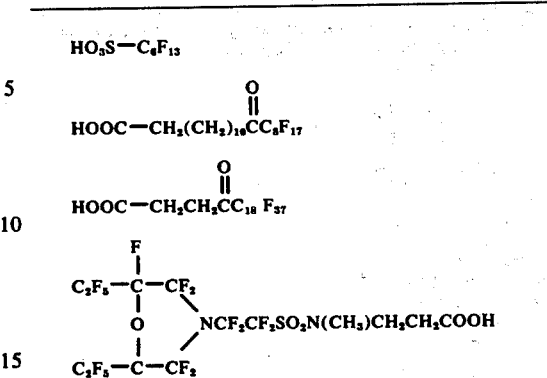

The Y-substituent of Formula 1, when present, is —H,—R¹, or M^{e+}, where M⁺ is a pharmaceutically acceptable organic or inorganic cation and R¹ is an aliphatic, cycloaliphatic or aromatic radical containing 1 to 24 carbon atoms, and where e is one, two, or three.

"Pharmaceutically-acceptable cation" refers to a cationic species which will not affect the non-irritating, non-toxic, cosmetically-formulatable properties of the compounds. Typical examples of inorganic cations are Na⁺, K115 and NH₄⁺; examples or organic cations are quaternary ions formed from triethylamine and triethanolamine. Examples of suitable Y-forming starting materials are given in the following Table III.

Table III

STARTING MATERIALS FROM WHICH THE Y-FORMING SUBSTITUENT MAY BE SELECTED

Inorganic Bases
  NH₄OH
  NaOH
  KOH
Inorganic Salts
  CaCl₂
  MgCl₂
  ZnCl₂ or zinc oxide
Alcohols
  HO—(CH₂)₇—CH₃
  HO—(CH₂)₉—CH₃
  HO—(CH₂)₁₁—CH₃
  HO—(CH₂)₁₃—CH₃
  HO—(CH₂)₁₅—CH₃
  HO—(CH₂)₂₁—CH₃

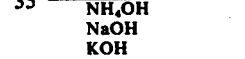

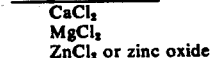

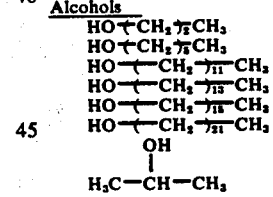

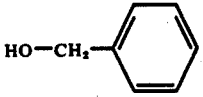

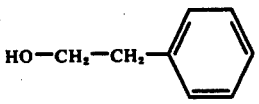

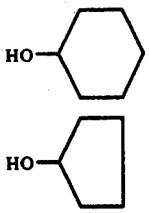

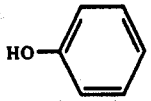

Table III-continued

STARTING MATERIALS FROM WHICH THE Y-FORMING SUBSTITUENT MAY BE SELECTED

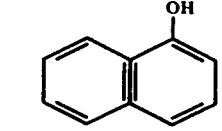

Amines
H₂N—CH₂—CH₃
H₂N—(CH₂)₅—CH₃
H₂N—(CH₂)₇—CH₃
H₂N—(CH₂)₁₇—CH₃
H₂N—(CH₂)₂₁—CH₃
HN—(C₄H₉)₂

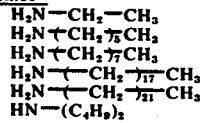

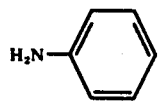

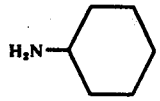

Table III-continued

STARTING MATERIALS FROM WHICH THE Y-FORMING SUBSTITUENT MAY BE SELECTED

(C₂H₅)₃N
(HOC₂H₄)₃N

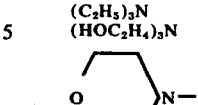

Mercaptans
HS—(CH₂)₂—CH₃
HS—(CH₂)₇—CH₃
HS—(CH₂)₁₇—CH₃

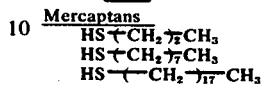

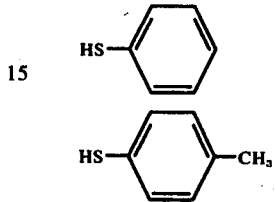

By selecting suitable starting materials from Tables I and II and in some cases including a starting material from Table III, the following representative compounds of Formula I may be prepared:

(1) HO—C(=O)—C₁₂H₂₄—C(=O)—O—CH₂—CH₂—N(C₂H₅)—SO₂C₈F₁₇

(2) HO—C(=O)—A*—C(=O)—O—CH₂—CH₂—N(C₂H₅)—SO₂C₈F₁₇

(3) H₁₇C₈O—C(=O)—C₁₀H₂₀—C(=O)—O—CH₂—CH₂—N(C₄H₉)—SO₂C₈F₁₇

(4) F₁₇C₈O₂S—N(C₂H₅)CH₂CH₂O—C(=O)—A*—C(=O)—O—CH₂—CH₂—N(C₂H₅)—SO₂C₈F₁₇

(5) H₇C₃HN—C(=O)—C₁₀H₂₀—C(=O)—NH—C₆H₄—OSO₂C₈F₁₇

(6) C₆H₅—HNC(=O)—A*—C(=O)—NH—C₆H₄—OSO₂C₈F₁₇ (with O—SO₂—C₈F₁₇ substituent)

(7) F₁₇C₈—(CH₂)₂—HN—C(=O)—A*—C(=O)—NH—C₆H₄—OSO₂C₈F₁₇

(8) HO—C(=O)—A*—C(=O)—NH—C₆H₄—OSO₂C₈F₁₇

(9) HO—C(=O)—A*—C(=O)—NH—(CH₂)₃C₈F₁₇

(10) HO—C(=O)—C₁₀H₂₀—C(=O)—NH—C₆H₄—OSO₂C₈F₁₇

(11) H₃C—C(=O)—HN—C₁₀H₂₀—NH—C(=O)—C₈F₁₇

-continued

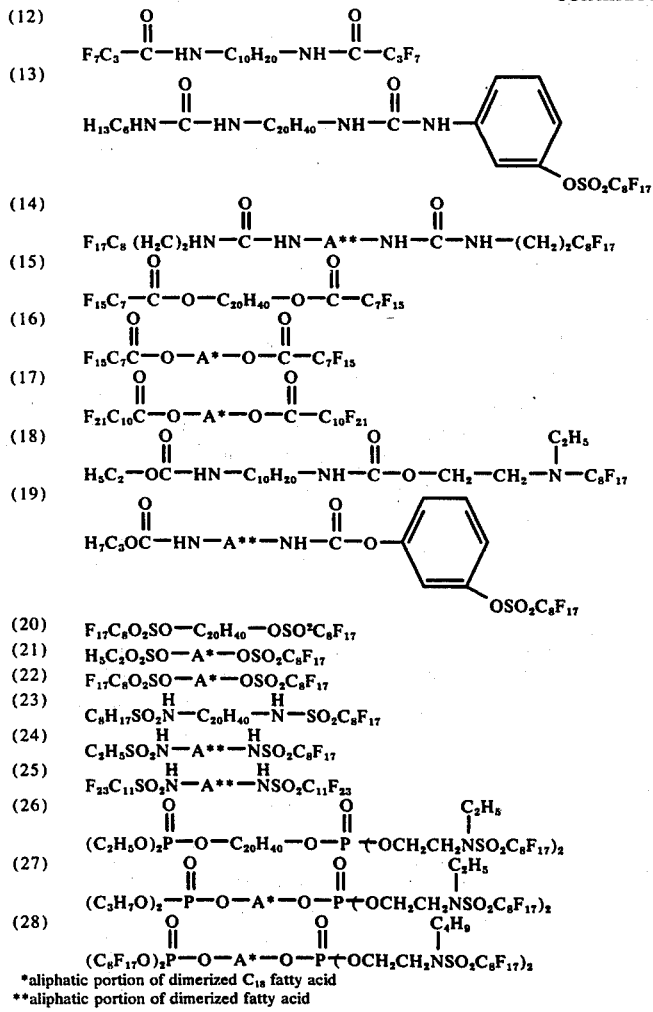

*aliphatic portion of dimerized $C_{18}$ fatty acid
**aliphatic portion of dimerized fatty acid The active dermal protective compounds of Formula I comprising the compositions of the invention contain from about 1 to 60 percent by weight of fluorine. The lower limit of about 1 percent is important because as the fluorine content is decreased below this amount, the compounds tend to lose their repellent properties. The upper limit of 60 percent is important because as the fluorine content is increased above this amount, the solubility of the compounds change, and they become more difficult to formulate with common pharmaceutical extending media.

The condensation reactions used to prepare compounds of the invention are carried out by mixing together the coreactants (i.e. compounds containing substituents A, X and Y) at one time or in sequence either by heat melting or in a suitable inert solvent such as benzene, toluene, xylenes, chloroform, dichloromethane, acetone, methyl ethyl ketone, diethyl ester, dibutyl ether or tetrahydrofuran. The reaction temperature may range broadly from room temperature (e.g., when using acid chlorides) to the boiling temperature of the solvent (e.g. when directly esterifying acids or alcohols). Generally the reaction temperature will be in the range of 20° to 150° C.

The synthesis of certain compounds of the invention may require the presence of an acid acceptor (e.g. an organic or inorganic base), condensing aid or catalyst to facilitate the reaction. Typical catalyst which may be used include trifluoromethane sulfonic acid, p-toluenesulfonic acid and hydrochloric acid for ester formation; and catalyst such as dibutyl tin diacetate, stannous octoate, lead octoate and cadmium octoate for urethane and urea reactions.

Condensing aids such as dicyclohexylcarbodiimide as well as acid chloride intermediates prepared with $POCl_3$ and $SOCl_2$ are useful in ester and amide formation.

A particularly useful process for preparing certain ester compounds of the invention involves the direct esterification of an acid or alcohol with a fluorocarbon-containing material with the appropriate functional group to form the ester linkage, using a strong cation (acid) exchange resin catalyst. The condensation reaction is coupled with the azeotropic distillation of water out of the reaction system with a solvent such as xylene.

Reaction times for preparing compounds of the invention may vary from ½ to 30 hours, depending on whether a catalyst or condensing aid is used. The direct esterification reaction described above is generally complete in 4 to 21 hours.

The yields of product from the condensation reactions can vary with the number of washings, neutralizations or other purification steps which must be carried out, but are generally between 65 and 100 percent by weight of the starting materials.

The amount of starting materials used may vary with the mode of preparation of the final products. Generally the equivalence ratio of the A-forming coreactant to the X-forming fluorocarbon coreactat and/or the Y-forming coreactant is in the range of about 20 to 0.5. The equivalence ratio of starting materials must, of course, be suitably adjusted in order to obtain a final product having the necessary fluorine content.

Most of the coreactants used to form the dermal protective agents of Formula I are commercially available materials. Due to the nature of some of the coreactants, for example, polybasic acid which is a mixture of di-, tri-, tetra-, penta-and hexacarboxylic acids, multiple products may be formed in some cases rather than a single pure product.

The physical appearance of the product defined by Formula I range from highly visious syrups to thick greases or glassy solids. In general, a waxy or greasy material is obtained. The products usually have melting points below 100° C., and in the range of about 40° to 80° C. The compounds are highly to moderately soluble in most organic solvents, occasionally requiring slight heating. Following dissolution by heating in various solvents such as lower alkanols, a number of products often form a gel-like solution upon cooling. The products are insoluble in water, but are readily emulsified with water.

The preferred dermal protective agents of this invention are the fluorocarbon-containing esters and amides prepared from polycarboxylic acids containing 8 to 108 carbon atoms, and the fluorocarbon-containing ureas and urethanes prepared from diisocyanates containing 8 to 108 carbon atoms. The preferred esters and amides are represented by the following formulas:

Formula 2a where A, X, Y, $n$ and $n'$ are as defined above in Formula 1. $n$ is an integer from 1 to 10; Z' is —NH— or —O—; and

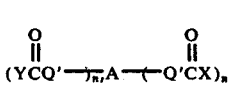

Formula 2b where A, X, Y, $n$ and $n'$ are as defined above in Formula 1, and Q' is —NH— or —O—.

The preferred urea and urethane compounds are represented by the following formula

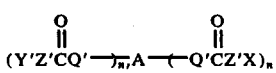

Formula 3 wherein A, $n$ and $n'$ are as defined above in Formula 1; Y' is —H or —R where —R is an aliphatic, cycloaliphatic or aromatic radical containing 1 to 24 carbon atoms; Z' is —NH— or —O—; and Q' is —NH— or —O—.

Compounds of Formulas 2a and 2b may contain mixtures of ester and amide linkages in the same product. Likewise, compounds of Formula 3 may contain mixtures of urea and urethane linkages in a single product.

Compounds of Formulas 2a and 2b comprise a group of novel compounds possessing unique substantive and oil and water repellent properties.

Especially preferred compounds of Formulas 2a and 2b are those wherein the A substituent is derived from the commercially available dimer and polybasic acids. These acids are derived from the dimerization or polymerization of $C_{18}$ fatty acids. Thus, dimer acid is believed to have the following structure

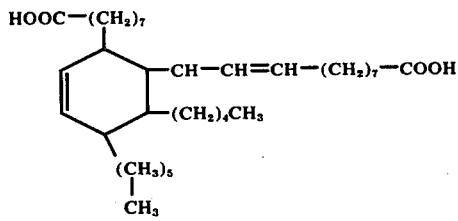

The higher analogues of polymerized $C_{18}$ fatty acid contain 3 or more carboxylic acid groups.

The especially preferred fluorocarbon esters and amides of the invention are the partially esterified and amidated dimer and polybasic acids and their salts, and having the following structure:

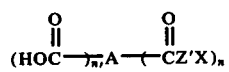

Formula 4 where A is a aliphatic saturated or unsaturated aliphatic or cycloaliphatic radical containing 34 to 108 carbon atoms; Z' is — NH — or — O —; X' is

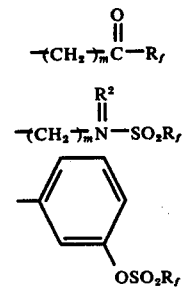

where $R^2$ is —H or an alkyl radical containing 1 to 8 carbon atoms; $R_f$ is a fluorinated, saturated, monovalent, aliphatic radical of 3 to 20 carbon atoms; $m$ is an integer from 1 to 12; $n$ is an integer from 1-9 designating the same or different

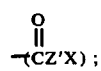

$n'$ is an integer from 1-9 and the sum of $n$ and $n'$ is 2 to 10.

The especially preferred esters and amides of Formula 4 contain 10 to 45 percent by weight of fluorine.

The fluorocarbon ureas and urethanes of Formula 3 which are especially preferred are the fully reacted products of the dimer diisocyanate (commercially available as General Mills Brand DDI ® 1410) having the following structure:

Formula 5 where A is a saturated aliphatic radical having 36 carbon atoms; X' is as defined in Formula 4; Q' is — NH — or — O —; $n$ is 2 designating the same or different

The perfluorocarbon ureas and urethanes of Formula 5 contain 25 to 45 percent by weight fluorine.

It is presently preferred that the fluorocarbon containing coreactant used to form the preferred fluorocarbon esters, amides, ureas, and urethanes of Formulas 4 and 5 contain a fluorocarbon group having a chain of eight perfluorocarbon atoms. Especially preferred perfluorocarbon groups are:

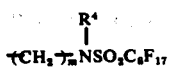

and

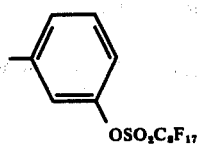

where $R^4$ is $-CH_3$, $-C_2H_5$, or $-C_4H_9$, and $m$ is an integer from 1 to 12.

The dermal-protective agents and compositions of the invention provide long-lasting oil-, water- and detergent-repellent coatings for the skin. These materials are effective in preventing or reducing contact of the skin with chemical irritants such as those found in detergents, disinfectants, machine oils, deodorants, bleaches, urine and other potentially skin-damaging compositions.

The dermal protective compositions and agents of the invention are substantive to skin and resist removal by mild abrasion and common irritant solutions. However, the materials may be removed, if desired, by aggressive abrasion in conjunction with detergent solution. The substantivity of the dermal-protective agents and compositions of this invention was determined in one manner by applying the materials to the surface of pigskin gelatin substrates. (The preparation of the gelatin substrate is described in detail in Examples below). The treated substrates were assayed spectrophotometrically to determine the amount of dermal protective agent present before any challenge. The treated substrates were then immersed for two to five hours in various irritant solutions. After this extremely long exposure to the irritant the substrates were again assayed spectrophotometrically and the percent loss of dermal protective agent from the substrate was determined. (This test is defined in greater detail in Example 12 below). Dermal-protective agents of the present invention were generally found to have less than 50% wash-off from the gelatin surfaces with the irritant solutions tested. These data indicate the extreme tenacity with which these materials adhere to proteinaceous surfaces.

The substantivity of the dermal-protective agents as well as their repellent properties toward various chemical irritants were determined by applying the protective agents alone or in a cosmetic formulation to the surface of raw pigskin and then measuring photograhically or visually the contact angle formed when droplets of irritant solutions were applied to the treated pigskins. Contact angles were measured both before and after the treated pigskins were subjected to a pressurized detergent flood. It was found that, both before and after flooding with detergent solutions, agents of the invention exhibited good repellent properties as evidenced by the large contact angles which were formed by droplets of irritant solution contacting the treated pigskin.

The pharmaceutical extending media comprising the dermal-protective compositions of the invention are conventional ingredients commonly used in the cosmetic art to formulate materials into lotions, creams, gels and the like for application to the skin. The active dermalprotective agents described hereinabove have the desirable property of being readily formulable with conventional ingredients using well-known techniques. Typical pharmaceutical extending media for use according to the present invention are those materials used to form an emulsion-type preparation. An emulsion formulation is one in which the active protective ingredient is combined with an emulsifying agent, such as triethanolamine stearate or glycerol monostearate; extending aids, such as lanolin, cetyl alcohol, stearyl alcohol, glycerol, sorbitol, mannitol and various oils. Other pharmaceutically acceptable ingredients such as buffering agents, opacifying agents, fragrances and preservatives may also be included in the dermal-protective compositions of the invention.

The dermal-protective agents of the present invention can be formulated singly or in combination into cosmetic creams and lotions. Since these agents manifest their protective properties by providing a physical barrier to irritants and not by chemical interaction with the irritant, it is not critical that the agents be used in pure form. The dermal protective agent is present in the composition in an amount ranging from 1 to 20 percent by weight of the composition, and preferably between 2 and 10 percent by weight of the composition.

By adding ultraviolet screening agents such as glyceryl p-aminobenzoate, menthyl salicylate and butyl p-hydroxycinnamate, a durable sun-burn preventative formulation is made possible which is not removed by exposure to water.

By incorporating compatible therapeutic agents into pharmaceutical extending media of the compositions of the invention, preparations having advantageous topical therapeutic action are provided. For example, bactericides such as hexachlorophene can be used to reduce the bacterial flora of the skin. Antibacterial and antifungal agents such as iodochlorohydroxyquinoline, salicyclic acid and cetyl pyrridinium chloride may also be included in compositions of this invention.

Compositions of this invention also furnish protection against contact allergies, diaper rash and the like.

Particularly preferred dermal-protective compositions of the invention are described in detail in the examples which follow.

EXAMPLES

The following non-limiting examples are illustrative of the preparations of the skin-substantive, skin-barrier compositions and agents of the invention, and their effectiveness as oil, water, detergent and solvent-repellent coatings which resist removal by abrasion and contact with various irritants.

In some of the examples the materials listed below are referred to by their trademark or by trade names. For reference purposes the compositions of these materials are given below:

Amberlyst ® 15— Macroreticular cation exchange resin
— Chemical structure - styrene-divinylbenzene resin
— Ionic Functionality - $RSO_3H$
— Porosity - 32%
— Mesh - 20-30
— Exchange Capacity - 4.9 meq. per gram Available from Rohm and Haas Company, Philadelphia, Pennsylvania Alconox ® — Wetting agent and detergent
— Phosphate Analysis — 7.3% phosphorus (by weight).

Phosphate analysis calculated as tri-sodium phosphate. 38.8% Note : Alconox contains no tri-sodium phosphate.

Made by Alconox, Inc., New York, N.Y. 10003 and available from Curtin Scientific Company.

Carbopol ® 940 — Water soluble resin
— Chemical Structure - carboxy vinyl polymer
— Approximate Molecular Weight - 4,000.000
— Cosmetic thickening agent Available from the B. F. Goodrich Chemical Company, 6100 Oak Tree Boulevard, Cleveland, Ohio 44131.

DDI ® Brand Diisocyanate 1410 — Aliphatic diisocyanate
— Chemical Structure — OCN —D—NCO, where D is a 36-carbon hydrocarbon radical
— Physical Form — clear, amber low viscosity syrup
— Molecular Weight — 600
— Equivalent Weight — 300
— NCO Content (%)— 14

Chemical Reactivity — reacts with materials containing active hydrogen atoms
— Solubility — soluble in a broad range of polar and non-polar solvents
— Information available from General Mills Company Technica Bulletin IC 1-72 and IC 3-72

Available from General Mills Co., 4620 W. 77th St., Minneapolis MN

Empol ® 1056A Polybasic Acid — Polymerized fatty acid, aliphatic polycarboxylic acid
— Physical Form - amber-colored, viscous syrup
— Composition
~1% monobasic acid
~59% dibasic acid
~40% polybasic acid
— Estimated Carboxyl Fuctionality — 2.65–2.75
— Acid Value — 188–192 (mg KOH/gm)
— Saponification Value — 188–192 (mg (KOH/gm)
— Additional date available from Emery Technical Bulletin No. 204

Available from Emery Industries, Inc., Carew Tower, Cincinnati, Ohio 45202

Hystrene ® 3695 — Essentially a dicarboxylic acid produced by the polymerization of C-18 fatty acids
— Physical Form — light yellow viscous syrup
— Composition
~1% monobasic acid
~95% dibasic acid
~4% tribasic acid
—Equivalent Weight 283–289
— Acid Value — 194–198 (mg KOH/gm)
— Saponification Value — 198–202 (mg KOH/gm)
— Further information form Humko Products Chemical Division Technical Bulletins SAI-4, 6 and 8

Available from Humko Products Chemical Division, White Station Tower, Memphis, Tennessee 38010

Hystrene ® 5460 — Mixture of polycarboxylic acids from the polymerization of C-18 fatty acids
— Physical Form — dark amber, quite viscous syrup
— Composition — Trace of monobasic acid
~40% dibasic acid
~60% trimer acid
— Molecular Weight - approx.) of the C-54 tribasic acid is 845
— Acid Value — 182–190 (mg KOG/gm)
— Saponification Value — 190–198 (mg KOH/gm)
— Solubility — soluble in most polar and non-polar solvents Available from Humko Products Chemical Division (address above)

Kind and Knox Gelatin 1312

Composition: Gelatin obtained by porkskin by the acid process.

General Characteristics: Off-white, granular solid
Basic properties:

| | |
|---|---|
| pH | 5.1 – 5.8 |
| Ash | 0.2% max. |
| Moisture | 12% max. |
| Copper | 5 p.p.m. max. |
| Iron | 20 p.p.m. max. |
| Isoionic point | 9.0 – 9.3 |
| Nitrate (as $NO_2$) | 10 p.p.m. max. |
| Viscosity (6.66% soln. at 60° C.) | 50 – 60 mp |
| Particle Size Distribution: | |
| Retained by 6 mesh | Less than 2% |
| Retained by 20 mesh | 58–80% |
| Retained by 40 mesh | 80–95% |
| Retained by 60 mesh | 94–100% |
| Retained by 100 mesh | 98–100% |
| Passed by 100 mesh | Less than 2% |

EXAMPLE 1

Preparation of: 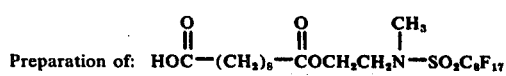

A 250 ml single-neck flask equipped with a magnetic stirring bar and reflux condenser fitted with a Dean-Stark water trap was charged with 8.09 g (0.08 equiv.) of sebacic acid, 22.3 g (0.04 equiv.) of N-methyl perfluorooctanesulfonamidoethyl alcohol, and 1.5 g Amberlyst ® 15 cation exchange resin (Mallinkcrodt, 4.9 mequiv./g) in 50 ml xylenes. The mixture was stirred and refluxed on a heating mantle for 12 hours, at which time an infrared spectrum of the product indicated the reaction was complete. Approximately 0.8 ml water was collected (0.72 ml, theoretical). Chloroform was used to dilute the mixture, and the solubles were decanted from the resin catalyst. Evaporation of the solvents in vacuo with heating on a hot water bath left 24.0 g of a beige-colored solid with a melting range of 82°–88° C. The product was soluble, with warming, in acetone and dichloromethane, and partially soluble in isopropyl alcohol.

EXAMPLE 2

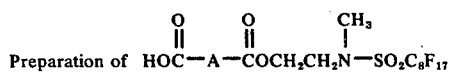

Preparation of HOC—A—COCH$_2$CH$_2$N—SO$_2$C$_8$F$_{17}$ (with O, O, CH$_3$ groups)

where A = the aliphatic portion of dimer acid.

A two liter three-necked flask equipped with a large magnetic stirring bar and a reflux condenser fitted with a Dean-Stark water collector was charged with 145.0 g (0.5 equiv.) of dimer acid (Hystrene ® 3695, acid equiv. wt. 290), 139.3 g (0.25 equiv.) of N-methyl perfluorooctanesulfonamidoethyl alcohol and 14.3 g Amberlyst 15 ® cation exchange resin in 290 ml xylenes. The reaction mixture was refluxed on a heating mantle with vigorous stirring for two hours, at which time approximately 4.2 ml water was collected. Also at this time, an infrared spectrum of the reaction product showed the reaction to be about 90% complete, as indicated by the ratio of the ester carbonyl absorption at 1740 cm$^{-1}$ to the acid carbonyl absorption at 1710 cm$^{-1}$. Infrared spectra of the reaction product at six and eight hours indicated nearly 100% completion of the reaction (ester carbonyl: acid carbonyl absorpton was 1:1) with approximately 5.5 ml water collected (4.5 ml, theoretical) at the eight hour point when the reaction was stopped.

The mixture was diluted with xylenes, filtered with suction on a Buchner funnel, and the filtrate evaporated on a hot water bath in vacuo using a rotary evaporator. An amber-colored grease (283 g) with a melting range of 51°–55° C was obtained. The material was very soluble in chloroform and acetone, and isopropanol with warming. A gel formed upon cooling of the isopropanol solution.

EXAMPLE 3

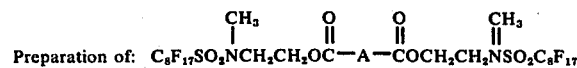

Preparation of: C$_8$F$_{17}$SO$_2$NCH$_2$CH$_2$OC—A—COCH$_2$CH$_2$NSO$_2$C$_8$F$_{17}$ where A is the aliphatic portion of dimer acid.

Into a two-neck 500 ml flask equipped with a magnetic stirring bar and reflux condenser fitted with a Dean-Stark water trap were placed 23.2 g (0.08 equiv.) dimer acid (Hystrene 3695, acid equiv. wt. 290), 44.6 g (0.08 equiv.) of N-methyl perfluoroocatanesulfonamidoethyl alcohol, and 3.4 g Amberlyst ® 15 cation exchange resin in 115 ml xylenes. The reaction mixture was vigorously stirred and refluxed on a heating mantle for 5.5 hours at which time an infrared spectrum showed the ester carbonyl:acid carbonyl ratio of the reaction product to be roughly 75:25. The refluxing was allowed to continue for a total of 21 hours, at which point at infrared spectrum showed only an ester carbonyl absorption at 1750 cm$^{-1}$. The semi-hard brown wax obtained (62.6 g) after filtration and evaporation of solvent had a melting range of 49°–57° C., and was readily soluble in dichloromethane, acetone and warm isopropanol. The isopropanol solution gelled upon cooling.

EXAMPLE 4

Preparation of: A(COCH$_2$CH$_2$ NSO$_2$C$_8$F$_{17}$)$_n$ where A is the aliphatic portion of polybasic acid; the average n value is 2.65–2.75.

Into a single-neck 250 ml flask equipped with a magnetic stirring bar and a reflux condenser fitted with a Dean-Stark water trap were placed 20.5 g (0.1 equiv.) of Empol ® 1056A polybasic acid (acid equiv. wt. 295 and estimated carboxyl functionality of 2.65–2.75), 55.7 g (0.1 equiv.) of N-,methyl perfluorooctanesulfonamidoethyl alcohol and 4.3 g. Amberlyst ® 15 cation exchange resin in 100 ml xylenes. The mixture was vigorously stirred and refluxed on a heating mantel for 12 hours at which time 1.3 ml water was collected and an infrared spectrum of the reaction product showed an ester carbonyl:acid carbonyl ratio of about 75:25. At this point, 1.0 g of additional Amberlyst ® 15 catalyst and 3.5 g of additional N-methyl perfluoroocatesulfonamidoethyl alcohol were added. An additional seven hours of refluxing followed by an infra-red spectrum of the product indicated that the reaction was complete, as evidenced by a single ester carbonyl absorption at 1740 cm$^{-1}$. An amount of water totaling 1.6 ml (1.8 ml, theoretical) was collected over this period. After decantation of the warm solution from the resin catalyst, and evaporation of the solvents in vacuo on a hot water bath using a rotary evaporator, a semi-hard, but deformable brown wax (75.0 g) was obtained with a melting range of 53°–58° C. The wax was very soluble in acetone, dichloromethane, isobutyl acetate, and warm ispropanol. The isopropanol solution gelled on cooling.

EXAMPLE 5

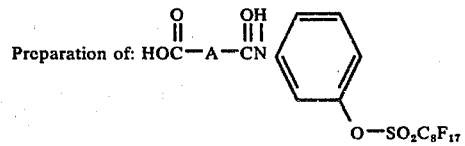

Preparation of: HOC—A—CN (with O, OH groups and phenyl ring with O—SO$_2$C$_8$F$_{17}$)

where A is the aliphatic portion of dimer acid.

Into a three-necked 250 ml flask equipped with a reflux condenser, a gas inlet connector, magnetic stirring bar, and dropping funnel were placed 11.4 g (0.04 equiv.) of dimer acid (Hystrene ® 3695, acid equiv. wt. 285) in 5 ml pyridine (0.06 equiv.) and 50 ml toluene. To this stirred solution at room temperature was added dropwise 2.2 ml (0.03 equiv.) of thionyl chloride in 25 ml toluene. After the addition, with an accompanying exotherm and the formation of a white precipitate, the mixture was refluxed on a heating mantle for 30 minutes, and then, with continued vigorous stirring and heating (approx. 110° C), a stream of nitrogen was swept through the system for several minutes. To the stirred warm mixture in the reaction flask was added a warm solution of 11.8 g (0.02 equiv.) of m-aminophenolperfluorooctanesulfonate in 25 ml toluene. When the addition was complete, the mixture was refluxed for 0.5 hours after which it was allowed to stand at room temperature for several days and then refluxed for 2 additional hours.

The reaction mixture was filtered with suction on a Buchner funnel and the solid residue (pyridine hydrochloride) was washed several times with toluene. Solvent from the filtrate was removed by heating on a hot water bath and evaporation in vacuo on a rotary evaporator. The residue after evaporation was taken up in 150 ml diethyl ether and washed in a separatory funnel with 50 ml saturated sodium chloride followed by 50 ml saturated sodium bicarbonate and finally with 50 ml water. Evaporation of the solvent in vacuo left a dark brown, syrupy solid (15.5 g) which melted at 30°–40° C and which was readily soluble in chloroform, acetone, and isopropanol. An infrared spectrum of the product showed the presence of a carboxyl carbonyl absorption at 1725 cm$^{-2}$, an amie NH absorption at 3300 cm$^{-1}$ and amide I and II carbonyl absorptions at 1680 and 1540 cm$^{-1}$, respectively. The acid:amide (I) carbonyl ratio was approximately 1:1.

EXAMPLE 6

Preparation of:

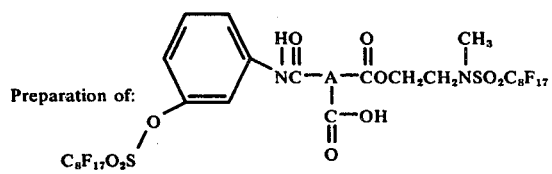

where A is the aliphatic portion of trimer acid.

A three-neck 1000 ml flask equipped with a reflux condenser, a gas inlet connector, dropping funnel, and a magnetic stirring bar was charged with 60.0 g (0.2 equiv.) of timer acid [Hystrene ® 5460, trimer: dimer (60:40) mixture, acid equiv. wt. approx. 300] in 23.9 g (0.3 equiv.) pyridine and 450 ml toluene. At room temperature, 14.9 g (0.13 equiv.) of thionyl chloride in 100 ml toluene was slowly added, while the solution was rapidly stirred. After the addition, the mixture was refluxed on a heating mantle for 15 minutes under a blanket of nitrogen. At the end of this time, a solution of 31.2 g (0.06 equiv.) N-methyl perfluorooctanesulfonamidoethyl alcohol and 35.4 g (0.06 equiv.) of m-aminophenylperfluorooctane sulfonate in toluene was added to the contents of the flask and the entire mixture refluxed on a heating mantle for 1.5 hours. The mixture was filtered with suction on a Buchner funnel and the solvents evaporated with heating in vacuo. The residue was taken up in 150 ml of diethyl ether and the solution was washed in a separatory funnel respectively with 100 ml of a saturated solution of sodium chloride, 100 ml of 1N hydrochloric acid, 100 ml of a saturated solution of sodium bicarbonate and finally with 200 ml of water. After drying the ether solution over anhydrous sodium sulfate, the ether was evaporated in vacuo with heating, leaving 110.0 g of a golden brown wax. The wax had a melting range of 48°–62° C and was very soluble in chloroform and isopropanol, and soluble, but turbid, in ethanol and isopropyl myristate. An infrared spectrum of the product showed absorptions for amide NH at 3250 cm$^{-1}$, and ester carbonyl at 1745 cm$^{-1}$. The ratio of carbonyl absorptions for acid:ester:amide was approximately 1.4:1.2:1.0.

EXAMPLE 7

Preparation of:

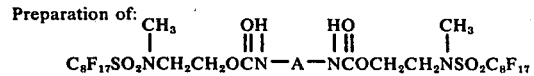

where A is the aliphatic portion of dimer diisocyanate.

A single-neck 250 ml flask equipped with a reflux condenser and a magnetic stirring bar was charged with 10.5 g (0.03 equiv.) of dimer diisocyanate (General Mills, DDI ® Brand 1410), 16.7 (0.03 equiv.) of N-methyl perfluorooctanesolufonamidoethyl alcohol and 1 ml of a 3% (wt. percent) acetone solution of dibutyl tin diacetate in 125 ml toluene. The solution was stirred and refluxed on a heating mantle for 4.5 hours, at which time an infrared spectrum of the reaction product showed the reaction to be complete, with the presence of a urethane NH absorption at 3350 cm$^{-1}$, a urethane carbonyl absorption at 1710 cm$^{-1}$, and no isocyanate absorption. After the solvent was evaporated with heating in vacuo, a tan-colored waxy solid (27.0 g) remained with a melting range of 90°–95° C. The product was readily soluble in chloroform, slightly soluble in acetone, and very slightly soluble in isopropanol.

EXAMPLE 8

Preparation of:

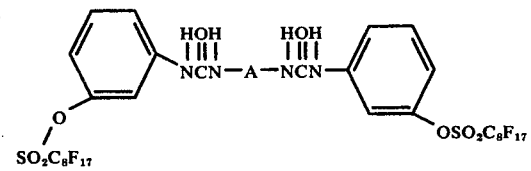

where A is the aliphatic portion of dimer diisocyanate.

Into a single-neck 100 ml flask equipped with a magnetic stirring bar and calcium chloride drying tube were placed 6.1 g (0.02 equiv.) of dimer diisocyanate (General Mills, DDI Brand 1410) and 11.8 g (0.02 equiv.) m-aminophenol perfluorooctane sulfonate. The mixture was stirred and heated in an oil-bath held at approximately 125° C. Within 15 minutes, the syrupy mixture turned from yellow to a reddish color, which progressively darkened to a deep orange-red at the end of the reaction. After two hours under the above conditions, an infrared spectrum of the reaction product was taken and the reaction shown to be complete, as indicated by the absence of an isocyanate absorption, and the presence of a urea NH absorption at 3250 cm$^{-1}$, and a urea carbonyl absorption at 1650 cm$^{-1}$. Upon cooling the reaction product to room temperature, a brittle, orange-red glassy solid was obtained with a melting range of 44°–50° C. It was very soluble in chloroform, warm ethanol, and warm isopropanol, and soluble in acetone, with the solution being cloudy. The material had a λmax in the ultraviolet of 272 nm (in chloroform).

EXAMPLE 9

Preparation of:

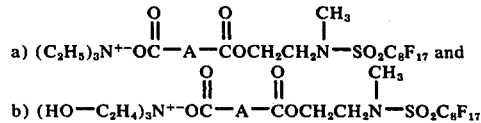

where A is the aliphatic portion of dimer acid a. One gram (0.91 milliequiv.) of the compound of Example 2 was dissolved in 5 ml of warm 100% ethanol in a small beaker. To this warm solution was added, with stirring, 0.11 g (1.1 milliequiv.) of triethylamine in 5 ml 100% ethanol. After cooling to room temperature, a tancolored ethanolic gel formed. An infrared spectrum of the product showed a broad absorption centered at around 1550 cm$^{-1}$, which is indicative of a carboxylate anion.

b. One gram (0.91 milliequiv.) of the compound of Example 2 was dissolved in 5 ml of warm 100% ethanol in a small beaker. To this warm solution was added, with stirring, 0.14 g (0.94 milliequiv.) of triethanolamine in 5 ml 100% ethanol. After cooling to room temperature, a tan-colored ethanolic gel formed. An infrared spectrum of the product showed a broad absorption centered at around 1560 cm$^{-1}$, which is indicative of a carboxylate anion.

EXAMPLE 10

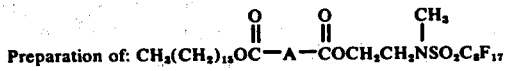

Preparation of: $CH_3(CH_2)_{15}OC-A-COCH_2CH_2NSO_2C_8F_{17}$ (with O, O, CH$_3$ groups as shown)

where A is the aliphatic portion of dimer acid

Into a single-neck, one-liter flask equipped with a large magnetic stirring bar and a reflux condenser fitted with a Dean-Stark water trap were placed 56.4 g (0.2 equiv.) of dimer acid [Hystrene ® 3695, acid equiv. wt. 282], 24.2 g (0.1 equiv.) 1-hexadecanol, 55.7 g (0.1 equiv.) N-methyl perfluorooctanesulfonamidoethyl alcohol, and 6.8 g Amberlyst ® 15 cation exchange resin in 200 ml xylenes. The reaction mixture was vigorously stirred and refluxed on a heating mantle for 6.0 hours, at which time 2.2 ml water was collected (theoretical: 3.6 ml) by azeotropic distillation. An infrared spectrum of the reaction product at this time showed the presence of a single, strong ester carbonyl absorption at 1730 cm$^{-1}$.

The liquid contents were decanted from the resin, and the solvent was evaporated with heating in vacuo leaving 131.0 g of a light brown, soft wax with a melting range of 58°–59° C. The product was soluble in acetone and warm isopropanol. The isopropanol solution gelled upon cooling. The compound rubbed smoothly into the skin, leaving a soft, non-tacky coating on the skin.

EXAMPLE 11

Preparation of:

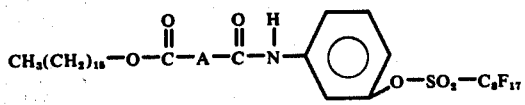

where A is the aliphatic portion of dimer acid.

Into a single-neck, 250 ml flask equipped with a magnetic stirrer and reflux condenser were placed 6.40 g (0.02 equivalents) of dimer acid chloride, 5.87 g (0.01 equiv.) of m-aminophenylperfluorooctanesulfonate, 4.84 g (0.01 equiv.) of hexadecanol, 1.80 g (0.022 equiv.) of pyridine and 75 ml of benzene. The reaction mixture was heated by means of an oil bath for about 4.5 hours at about 70° C during which time a white precipitate formed. The vessel as cooled and 75 ml of benzene were added and the whole mixture was washed with 150 ml of water. 50 ml of chloroform was then added and the organic solution was then washed twice with a total of 300 ml of water. The washed organic layer was dried and the solvent was removed in vacuo by evaporation to yield 13 g of a pale brown grease. The structure of the product was confirmed by infrared spectral analysis.

EXAMPLE 12

Water and aqueous solutions of detergent and ammonia were used to challenge the active dermal-protective agents of Examples 2, 5 and 8 following their application to a protein substrate.

The proteinaceous surface used for the controlled evaluation of the substantivity of these dermal-protective agents was pigskin gelatin. This proteinaceous surface was used as a model for human skin. The pigskin gelatin substrate was prepared using the following ingredients:

| | |
|---|---|
| Pig-skin gelatin (Kind and Knox 1312) | 300 g |
| 15% ® Saponin (surfactant) | 60 ml |
| Sorbitol - H$_2$O (1:2) | 30 ml |
| 3.7 % Formaldehyde | 22 ml |
| Water (Deionized) | 5408 ml |
| 1% Thymol | 30 ml |
| Total Weight = | 5850 g |

A liquid composition was prepared by mixing together the above ingredients. This liquid composition was singleslot coated on both sides of a cellulose triacetate film (5 mil thickness) under the following conditions:

| | |
|---|---|
| Flow rate | 190 ml/min. |
| Coating speed | 16 g/min. |
| Coating width | 8 ¾ in. |

The coating was air dried and the final coating (on one side) contained 104 mg. gelatin per square decimeter.

Solutions of the active dermal agents of Examples 2 and 8 in chloroform (10% w/v) were coated as thin films on one side of 1 × 3 inch strips of the pigskin gelatin prepared above. The coated strips were immersed, by hanging from a glass rod, into beakers containing respectively tap water, 1% aqueous Alconox ® detergent solution, and 1% ammonia/2% urea solution. The solutions were stirred during the test, and the strip coated with the product of Example 2 was withdrawn after 5 hours immersion in the tap water and 3 hours immersion in the detergent and ammonia solutions while the strip coated with the product of Example 8 was withdrawn after 16 hours immersion in water, 2.5 hours immersion in the detergent solution, and 4 hours immersion in the ammonia solution. The strips were lightly rinsed with water and air-dried. The coated surfaces were then analyzed either by multiple-internal reflectance infrared spectrophotometry or ultraviolet spectrophotometry (for the coating of Example 8). In the infrared analysis of the coating of Example 2, the intensity of the ester carbonyl absorption at 1755 cm$^{-1}$ was measured before and after each challenge. The relative percentage of loss or wash-off of the coating after each challenge was then calculated. For the coating of Example 8, the intensity of the absorption at 272 nm in the ultraviolet was compared before and after each challenge and the percentage of the coating removed by each solution was determined. The results were as follows:

RELATIVE PERCENT LOSS OF COATING AFTER CHALLENGE

| Coating | Water | 1% Alconox ® | 1% NH$_3$/2% Urea |
|---|---|---|---|
| Example 2 | 20.0 | 15.4 | 15.4 |
| Example 8 | 20.7 | 6.5 | 8.3 |

EXAMPLE 13

Solutions of the active dermal-protective agents of Examples 2, 3, and 4 were made up in isopropanol at a concentration of 5% (w/v). Each of the solutions was applied, using four strokes of a cotton swab, to the skin area on the top side of alternate fingers between the nail and second knuckle of a human volunteer. The alcohol was allowed to evaporate. Drops of decalin and then hexane were applied to each treated finger and to the untreated fingers with a syringe. The untreated fingers quickly gave rise to whitened spots and streaks due to the defatting action of the decalin and hexane on the lipids of the skin surface. The treated fingers showed some beading and run-off of the decalin and hexane. On the finger treated with the protective agent of Example 2, a slightly whitened streak appeared, while the fingers treated with the agents of Examples 3 and 4 showed no signs of whitening, even after six consecutive droplet applications. In view of the excellent penetration of decalin and hexane into fats and their ability to solubilize fatty materials, this test demonstrates the excellent protection against solvent penetration to the skin afforded by the dermal protective agents of this invention.

EXAMPLE 14

Coatings were applied to clean, raw pigskin in aliquots with a syringe from a 1% solution of the text material (in $CHCl_3$). Each coating contained approximately 0.25 g of test material per square inch of pigskin. Four test droplets, one each, of water, detergent (5% Alconox ® solution) solution, oil and hexadecane were then applied to the treated pigskin. Photographs were taken of the contact angles within 30 seconds after the droplet was applied to the treated pigskin. Each separate sample was then challenged with detergent solution or solvent. When the challenging agent was detergent solution, each sample was placed under a pressurized stream of warm (40° C) detergent (0.5% sodium dodecyl benzene sulfonate) and washed for one hour. The outlet of the pressurized stream of detergent solution (approximately 0.15 cm in diameter) was positioned approximately 0.25 cm above the surface of the coated pigskin and the flow rate was approximately 500 ml/min. When the challenging agent was a solvent, each sample was subjected to a continuous stream of the solvent wash stream (approximately 0.15 cm in diameter) was positioned approximately 0.1 cm above the sample surface. After each challenge the contact angles formed with the four test droplets were again measured photographically.

The pressurized detergent flood and the solvent wash were also meant to provide abrasive challenge to the coatings. The maintainance of a coating after such challenges was, therefore, indicative of abrasion resistance, as well as substantivity toward detergent and solvent wash of the materials tested.

A rating system was devised by assigning a point score to each contact angle value (for example, 0° = 1.5, 10° = 2.0, 20° = 2.5, 30° = 3.0, 40° = 3.5, 50° = 4.0, 100° = 6.5, etc.) and a total value ("comparative value") was obtained by adding together the point scores from each measurement. A higher number for the comparative value reflects higher substantivity and oil and water repellency compared to untreated pigskin.

The excellent substantivity and repellent properties of the dermal-protective agents are readily apparent from the data presented below.

MEASURED CONTACT ANGLES

|  | Ex. 2 average of (4 tests) | | Ex. 3 (1 test) | | Ex. 5 (1 test) | | Ex. 8 (1 test) | |
| --- | --- | --- | --- | --- | --- | --- | --- | --- |
| Initial | Degrees | (Rating) | Degrees | (Rating) | Degrees | Rating | Degrees | (Rating) |
| Water | 111 | (7.05) | 96 | (6.30) | 106 | (6.80) | 104 | (7.30) |
| Detergent | 84 | (5.70) | 62 | (4.60) | 78 | (5.40) | 95 | (6.25) |
| Nujol | 79 | (5.45) | 75 | (5.25) | 85 | (5.75) | 86 | (5.80) |
| Hexadecane | 68 | (4.90) | 60 | (4.50) | 90 | (6.00) | 94 | (6.20) |
| After Detergent Wash | | | | | | | | |
| Water | 90 | (6.00) | 37 | (3.35) | 62 | (4.60) | 73 | (5.20) |
| Detergent | 76 | (5.30) | 32 | (3.10) | 57 | (4.35) | 75 | (5.25) |
| Nujol | 89 | (5.95) | 79 | (5.45) | 71 | (5.05) | 79 | (5.45) |
| Hexadecane | 81 | (5.55) | 57 | (4.35) | 58 | (4.40) | 54 | (4.20) |
| After Heptane Wash | | | | | | | | |
| Water | 111 | (7.05) | 94 | (7.20) | 120 | (7.50) | 103 | (6.65) |
| Detergent | 78 | (5.40) | 65 | (4.75) | 79 | (5.45) | 79 | (5.45) |
| Nujol | 76 | (5.30) | 74 | (5.20) | 94 | (6.20) | 88 | (5.90) |
| Hexadecane | 58 | (4.40) | 83 | (5.65) | 74 | (5.20) | 82 | (5.60) |
| After Ethanol Wash | | | | | | | | |
| Water | 95 | (6.25) | 89 | (5.95) | 85 | (5.75) | 108 | (6.90) |
| Detergent | 75 | (5.25) | 80 | (5.50) | 42 | (3.60) | 64 | (4.70) |
| Nujol | 68 | (4.90) | 81 | (5.55) | 72 | (5.10) | 57 | (4.35) |
| Hexadecane | 48 | (3.90) | 55 | (4.25) | 60 | (4.50) | 50 | (4.00) |
| After Toluene Wash | | | | | | | | |
| Water | 106 | (6.80) | 103 | (6.65) | 117 | (7.35) | 113 | (7.15) |
| Detergent | 89 | (5.95) | 80 | (5.50) | 77 | (5.35) | 99 | (6.45) |
| Nujol | 80 | (5.50) | 76 | (5.30) | 78 | (5.40) | 99 | (6.45) |
| Hexadecane | 46 | (3.80) | 79 | (5.45) | 50 | (4.00) | 81 | (5.55) |
| Comparative Values* | 110 | | 103 | | 108 | | 115 | |

*Total of the Ratings from each measured contact angle. Comparative Value of untreated pigskin is 40

EXAMPLE 15

This Example illustrates the incorporation of the active dermal-protective agents of Example 2 into a typical pharmaceutical extending medium to form a protective cream. The cream was formulated with the following ingredients.

| Component | Quantity by Weight (Parts) |
| --- | --- |
| Part A | |
| Stearic acid | 4.0 |
| Cetyl alcohol | 0.5 |
| Lanolin (anhydrous) | 2.0 |
| Monoperfluoro ester of Example 2 | 3.6 |
| Part B | |

| Component | Quantity by Weight (Parts) |
|---|---|
| Deionized water | 82.0 |
| Carbopol ® 940 (B. F. Goodrich Co.) | 0.2 |
| Triethanolamine (98%) | 1.0 |
| Methyl Paraben | 0.2 |

Part B was prepared by first placing the deionized water in a 500 ml beaker and then stirring it rapidly with an air-driven stirrer while the Carbopol 940 was slowly added. After the Carbopol ® was dissolved, the triethanolamine and methyl paraben were added with stirring. The mixture was then heated to 75° C in a warm water bath. The ingredients of Part A were mixed together and heated to 75° C in a warm water bath and then added to Part B at 75° C with stirring. Following the addition of Part A to Part B the warm water bath was removed. Stirring was continued until the temperature of the mixture had dropped to room temperature, at which time a thick, white cream resulted which was applied to the skin leaving no tackiness and which imparted a pleasant feel when rubbed into the skin.

After application of the cream to the skin, a water-, detergent- and oil-repellent coating was left on the skin, which remained in place even after repeated soap and detergent washings.

EXAMPLE 16

A cream base containing the active dermal protective agent of Example 6 was formulated using the same cosmetic base components and amounts and the same procedure as in Example 11. A thick, white cream was obtained, which was cosmetically elegant, easy to apply to the skin and smooth to the touch. The composition displayed long-lasting repellent properties toward water, various detergents, and oils when applied to the skin.

EXAMPLE 17

Two representative dermal-protective compositions were formulated using the product of Example 2, according to the method described in Example 15.

These compositions were designed especially as urine repellent compositions to provide protection against "diaper rash" and other forms of irritation caused by contact with urine. The ingredients of each formulation are given below. In each case the water and oil phases were prepared separately and heated to 70°–75° C. The water phase was then added to oil phase with mixing and cooling to achieve the final cream or lotion composition.

| Formulation A (Cream) Ingredient | Percent by weight |
|---|---|
| Water phase | |
| Product of Example 2 (active urine repellent) | 6.0 |
| Glycerol monostearate | 1.5 |
| Stearic acid | 15.0 |
| Cetyl alcohol | 1.5 |
| Glycerine | 1.5 |
| H₂O | 53 to 58 |
| Oil phase | |
| Triethanolamine | .750 |
| Methyl Paraben | .15 |
| Propyl Paraben | .15 |
| Methyl benzalkonium chloride | .10 |
| Imidazolinoyl urea compound | .30 |
| ZnO | 5–10 |
| Formulation B (Lotion) Ingredient | Parts by weight |
| Oil phase | |
| Glycerol monostearate | 4 |
| Lanolin oil | 2 |
| Stearic acid | 2 |
| Product of Example 2 | 6 |
| Glycerin | 10 |
| Water phase | |
| Water | 74.3 |
| Triethanolamine | 7 |
| Parabens (methyl and propyl) | .30 |
| Imidazolinonyl urea compound | .3 |
| Methylbenzalkonium chloride | .1 |

An additional formulation using the product of Example 2 was prepared for use as a urine repellent composition. This composition was of the oil type in contrast to the oil-water emulsion type formulations A and B above. This oil composition was prepared by mixing together the following ingredients at a temperature of 70° C followed by cooling to room temperature while stirring.

| Formulation C (Oil) Ingredients | Parts by weight |
|---|---|
| Mineral Oil | 42.5 |
| Decyl Oleate | 29.29 |
| Isopropyl myristate | 14.25 |
| Polydiester of short chain fatty acids | 4.5 |
| Lanolin oil | 4.5 |
| Product of Example 2 | 5 |

EXAMPLE 18

Three typical compositions were prepared for use as dermal protective hand creams. These compositions utilized the product of Example 2 as the active dermal protective agent and were prepared according to the method of Example 15. The formulations are set out below. Formulation A contains a moisturizer additive to provide a composition with both repellent and moisturizing properties.

| Formulation A Ingredients | Parts by Weight |
|---|---|
| Oil phase | |
| Product of Example 2 | 4 |
| Extract of lanolin alcohols | 8 |
| Acetylated lanolin Alcohols | 1 |
| Stearic acid | 2.5 |
| Propyl paraben | 0.15 |
| Gycerol monostearate | 2.0 |
| Mineral Oil | 4.5 |
| Water phase | |
| Distilled water | 73.0 |
| Propylene glycol | 4.5 |
| triethanolamine | 1.0 |
| methyl paraben | 0.15 |
| Imidazolinoyl urea compound | 0.30 |
| Fragrance | .05 |
| FORMULATION B Ingredients | Percent by Weight |
| Oil Phase | |
| Product of Example 2 | 4.0 |
| Stearic Acid | 2.5 |
| Propyl Paraben | 0.1 |
| Gycerol Monostearate | 1.5 |
| Water Phase | |
| Distilled Water | 90.7 |
| Fragrance | .05 |
| Methyl Paraben | 0.15 |
| Triethanolamine | 1.0 |
| FORMULATION C Ingredients | Percent by Weight |
| Oil Phase | |
| Product of Example 2 | 8.0 |
| Propyl Paraben | 0.1 |
| Cetyl Alcohol | 0.25 |
| Sorbitan Monopalmitate | 2.5 |

| | |
|---|---|
| Propyl Gallate | 0.003 |
| Water Phase | |
| Distilled Water | 87.65 |
| 10% NaOH Solution | 0.2 |
| Ammonium Lauryl Sulfate | 0.5 |
| Methyl Paraben | 0.15 |
| Carbopol 940 | 0.15 |
| Citric Acid | 0.0018 |
| Fragrance | 0.5 |

EXAMPLE 19

To further illustrate the excellent substantivity and barrier properties of the dermal protective agents and compositions of the invention under warm detergent wash-off conditions, the following test was carried out. Large pieces of raw pigskin were washed lightly with soap and water (to remove excess surface fats), rinsed, lightly patted with tissue, and air-dried. Solutions (1% in chloroform) of the active dermal protective agents or cosmetic compositions containing them were applied with a cotton swab to the pigskin, resulting in coatings containing approximately 1 mg test material per square inch of pigskin. As a control, only the solvent was applied which contained no test material in some cases. Colored droplets of oil (Nujol), deionized water and detergent solution (0.5% sodium dodecyl benzene sulfonate) were applied to the treated and untreated pigskin, and the resulting contact angles were measured visually approximately 60 seconds after application. Scores were assigned according to a rating scale of 0 to 6 based on the magnitude of the contact angle formed between the droplet and the surface of the pigskin. The contact angles and their assigned ratings are as follows:

| Contact Angles | Rating |
|---|---|
| 100–120° | 6 |
| 90–100° | 5 |
| 60–90° | 4 |
| 40–60° | 3 |
| 20–40° | 2 |
| 1–20° | 1 |
| Spreading | 0 |

Each test material was given a pre-flood cumulative rating (sum of the three droplets) and then the treated and untreated pigskin surfaces were subjected to a one hour warm detergent flush as described in Example 14 with a 0.5% solution of sodium dodecyl benzene sulfonate. After a brief rinse with water and air drying, colored droplets of oil (Nujol), water and detergent were again applied to the surface of the treated and untreated pigskin. The contact angles formed were rated using the same scale given above, and the three ratings were added together to give a post-flood cumulative rating. The same procedure was repeated several times for each test material and results were computed by adding the individual ratings for each droplet (i.e. Nujol droplet, water droplet and detergent droplet.) The fractional numbers arise from scores intermediate between the whole numbers.

EXAMPLE 19

| | CUMULATIVE RATINGS | | |
|---|---|---|---|
| Test Material (Example No.) | Ave. Post-Flood Cum. Rating/X100 Ave. Pre-Flood Cum. Rating | Average Pre-Flood Cum. Rating | Average Post-Flood Cum. Rating |
| 1 | 80.6 | 14.4(4 tests) | 11.6 (4 tests) |
| 2 | 106.8 | 13.3(10 tests) | 14.2(10 tests) |
| 3 | 92.0 | 11.3(4 tests) | 10.4(4 tests) |
| 4 | 85.5 | 12.4(4 tests) | 10.6(4 tests) |
| 5 | 97.9 | 14.0(10 tests) | 13.7(10 tests) |
| Pigskin Control | 97.7 | 8.6(11 tests) | 8.4(11 tests) |
| 6 | 98.5 | 13.6(4 tests) | 13.4(4 tests) |
| 7 | 75.6 | 11.9(4 tests) | 9.0(4 tests) |
| 8 | 79.7 | 13.3(4 tests) | 10.6(4 tests) |
| 9-A | 91.7 | 13.3(3 tests) | 12.2(3 tests) |
| 9-B | 95.3 | 12.8(3 tests) | 12.2(3 tests) |
| 15 | 114.0 | 10.7(6 tests) | 12.2(6 tests) |
| 16 | 110.2 | 10.8(4 tests) | 11.9(4 tests) |
| Dimer Acid | 121.3 | 6.1 (8 tests) | 7.4(8 tests) |
| Dimer Diol | 168.4 | 3.8(4 tests) | 6.4(4 tests) |

When subjected to the above-described test, the dermal-protective agents and compositions of the invention preferably have an average pre-flood cumulative rating score of at least 10 and average retention of at least 70% of that score after flooding with detergent for one hour (i.e. post-flood cumulative rating/pre-flood cumulative rating × 100 > 69). The variability of properties and response of individual pigskins and areas on the same pigskin must be taken into account when evaluating the results of this test. Occasionally a particular pigskin surface may exhibit a variable degree of inherent repellency in the untreated state. For this reason it is desirable to repeat the test on a number of different pigskins in order to obtain a representative value for a particular test material.

What is claimed is:

1. In a dermal protective composition comprising a pharmaceutical extending medium and a protective amount of a fluorocarbon-containing active ingredient, the improvement comprising employing as said active ingredient a substantive dermally non-irritating compound of the formula

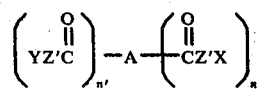

wherein
A is a polyvalent saturated or unsaturated, aliphatic or cycloaliphatic organic radical containing 8 to 108 carbon atoms;
Z' is —NH— or —O—;

X is —(W)$_d$R$_f$ where W is a bridging group free of isocyanate or isocyanate reactive groups, $d$ is a zero or one, and R$_f$ is a fluorinated, saturated, monovalent, aliphatic radical containing 3 to 20 carbon atoms in which the carbon atoms of the chain are substituted only by fluorine, chlorine or hydrogen atoms with no more than one hydrogen or chlorine atom for every two carbon atoms and the terminal carbon atom is perfluorinated, and in which a divalent oxygen or trivalent nitrogen atom, bonded only to carbon atoms can be present in the skeletal chain;

Y is —H, M$^{e+}$, or R$^1$ where R' is an aliphatic, cycloaliphatic or aromatic radical containing 1 to 24 carbon atoms;

M$^{e+}$ is a pharmaceutically acceptable organic or inorganic cation and $e$ is one, two or three;

$n$ is an integer from 1 to 10 designating the same or different

$n'$ is zero or an integer from 1 to 9 designating the same or different

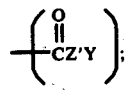

$n+n' = 2 - 10$; said compound containing from 1 to 60 percent by weight of fluorine.

2. A composition according to claim 1 wherein W is selected from the group consisting of:

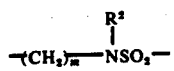 (1)

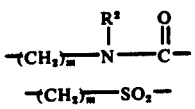 (2)

 (3)

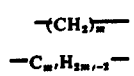 (4)

—(CH$_2$)$_m$— (5)

—C$_{m'}$H$_{2m'-1}$— (6)

(7)

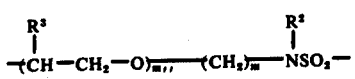 (8)

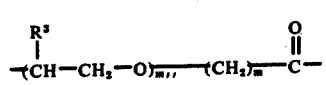 (9)

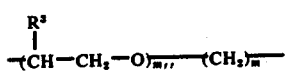 (10)

 (11)

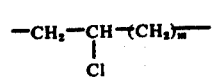 (12)

-continued

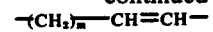 (13)

 (14)

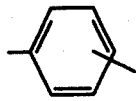 (15)

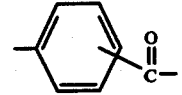 (16)

and

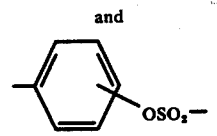 (17)

where
R$^2$ is H or an alkyl radical containing 1 to 8 carbons;
R$^3$ is H, —CH$_3$ or —C$_2$H$_5$,
$m$ is an integer from 1 to 12.
$m'$ is an integer from 2 to 12.
$m''$ is an integer from 1 to 24.

3. In a dermal protective composition comprising a pharmaceutical extending medium and a protective amount of a fluorocarbon-containing active ingredient, the improvement comprising employing as said active ingredient a substantive, dermally non-irritating compound of the formula

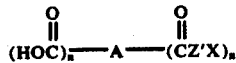

where A is a polyvalent saturated or unsaturated, aliphatic or cycloaliphatic organic radical containing 34 to 108 carbon atoms; Z' is —NH— or —O—; X is

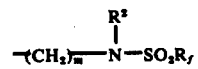

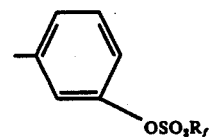

R$_f$ is a fluorinated, saturated, monovalent aliphatic radical containing from 3 to 20 carbon atoms in which the carbon atoms of the chain are substituted only by fluorine, chlorine or hydrogen atoms with no more than one hydrogen or chlorine atom for every two carbon atoms and the terminal carbon atom is perfluorinated, and in which a divalent oxygen or trivalent nitrogen atom, bonded only to carbon atoms, can be present in the skeletal chain; m is an integer from 1 to 12; R$^2$ is H or an alkyl radical containing 1 to 8 carbon atoms; n is an integer from 1 to 10 designating the same or different

$n'$ is zero or an integer from 1 to 9; said compound containing from 1 to 60 percent by weight of fluorine.

4. A composition according to claim 3 wherein X is

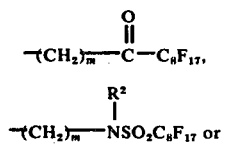

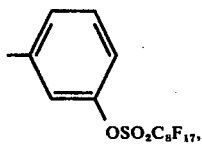

where $R^2$ is $-CH_3$, $-C_2H_5$, or $-C_4H_9$, and $m$ is an integer from 1 to 12.

5. In a dermal protective composition comprising a pharmaceutical extending medium and a protective amount of a fluorocarbon-containing active ingredient, the improvement comprising employing as said active ingredient a substantive, dermally non-irritating compound of the formula

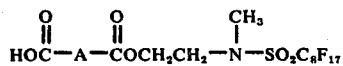

where A contains 34 carbon atoms and is the aliphatic portion of polymerized 18-carbon fatty acids.

6. In a dermal protective composition comprising a pharmaceutical extending medium and a protective amount of a fluorocarbon-containing active ingredient, the improvement comprising employing as said active ingredient a substantive, dermally non-irritating compound of the formula $$C_8F_{17}SO_2NCH_2CH_2OC-A-COCH_2CH_2NSO_2C_8F_{17}$$
(with $CH_3$ groups on N, and $O$ double bonds on C)

where A contains 34 carbon atoms and is the aliphatic portion of polymerized 18-carbon fatty acids.

7. In a dermal protective composition comprising a pharmaceutical extending medium and a protective amount of a fluorocarbon-containing active ingredient, the improvement comprising employing as said active ingredient a substantive, dermally non-irritating compound of the formula $$A(COCH_2CH_2NSO_2C_8F_{17})_n$$

where A contains 34, 51, 68, 85 or 102 carbon atoms and is the aliphatic portion of polymerized 18-carbon fatty acids, and $n$ is an integer from 2 to 6.

8. In a dermal protective composition comprising a pharmaceutical extending medium and a protective amount of a fluorocarbon-containing active ingredient, the improvement comprising employing as said active ingredient a substantive, dermally non-irritating compound of the formula

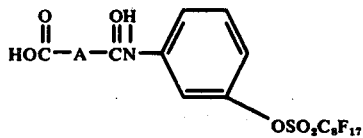

where A contains 34 carbon atoms and is the aliphatic portion of polymerized 18-carbon fatty acids.

* * * * *